United States Patent [19]
Luse et al.

[11] Patent Number: 5,620,320
[45] Date of Patent: Apr. 15, 1997

[54] SUBSTANTIALLY CONSTANT FORCE COIL SPRING USABLE IN EXTRAORAL ORTHODONTIC APPLIANCE

[76] Inventors: Steven O. Luse; Craig L. Jacobson, both of 1611A S. Melrose Dr., #16, Vista, Calif. 92083-5471

[21] Appl. No.: 435,087

[22] Filed: May 4, 1995

[51] Int. Cl.⁶ ........................................... A61C 7/00
[52] U.S. Cl. ..................................... 433/5; 433/21
[58] Field of Search ............................. 433/5, 21

[56] References Cited

U.S. PATENT DOCUMENTS

| | | | |
|---|---|---|---|
| 4,115,921 | 9/1978 | Armstrong | 433/5 |
| 4,226,589 | 10/1980 | Klein | 433/5 |
| 4,264,302 | 4/1981 | Wolk et al. | 433/5 |
| 4,553,933 | 11/1985 | Armstrong et al. | 433/5 |
| 4,553,934 | 11/1985 | Armstrong et al. | 433/5 |
| 4,849,032 | 7/1989 | Kawaguchi | 148/11.5 R |
| 4,872,836 | 10/1989 | Grove | 433/5 |
| 5,046,948 | 9/1991 | Miura | 433/21 |

*Primary Examiner*—Cary E. O'Connor
*Attorney, Agent, or Firm*—Jack C. Munro

[57] ABSTRACT

An orthodontic coil spring to be used within an extraoral orthodontic appliance where the coil spring is made of a superelastic, shape-memory alloy wire. The coil spring is to impart a substantially constant force over the entire range of deflection. The level of force is to be between 375 to 800 grams.

3 Claims, 2 Drawing Sheets

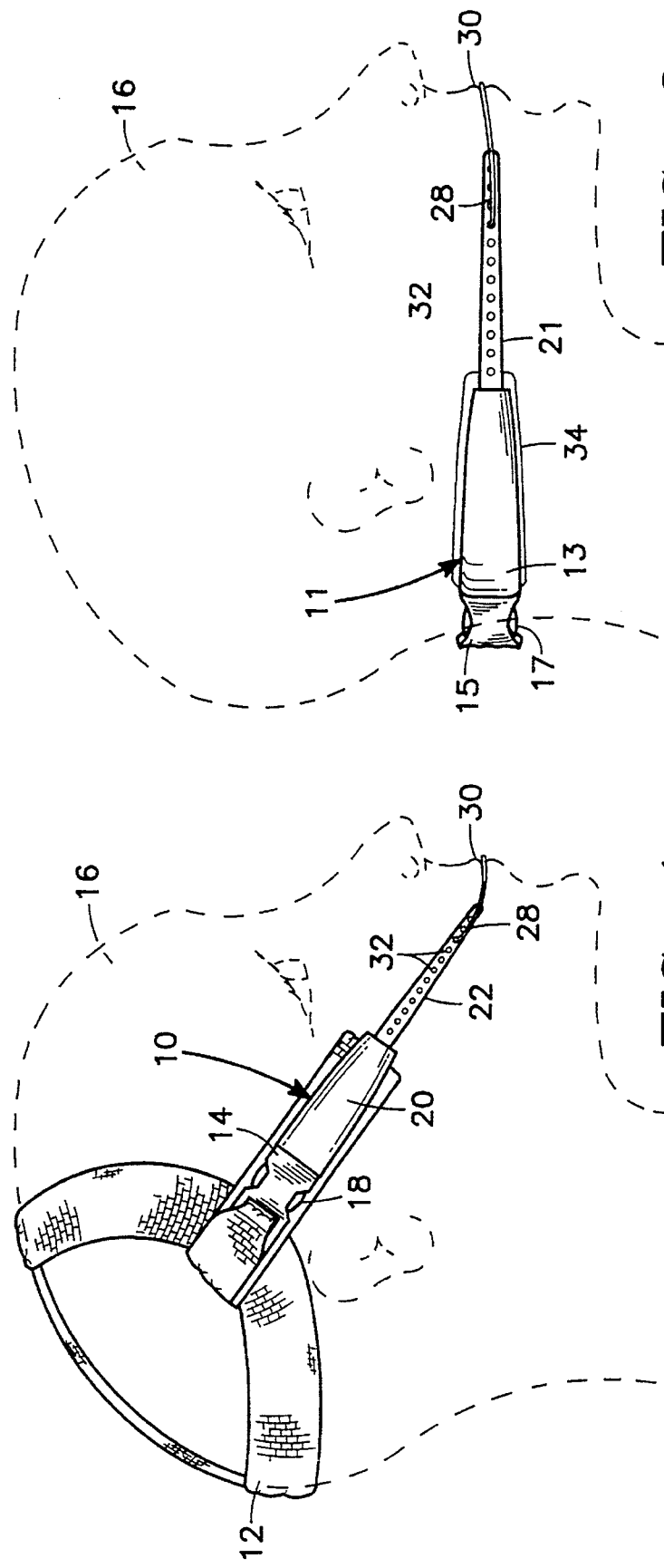
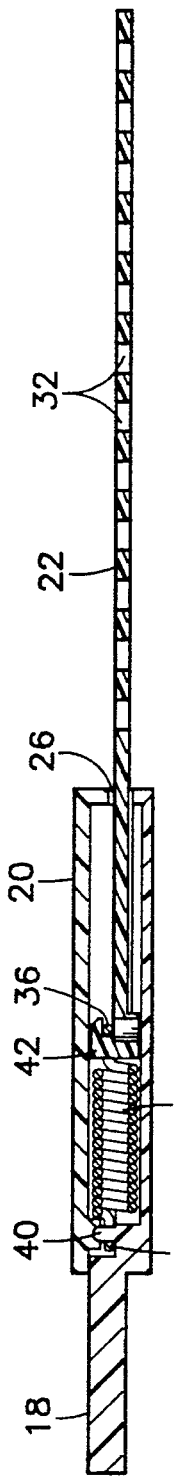

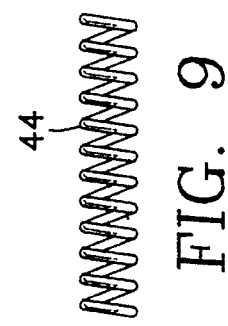
FIG. 8
FIG. 9
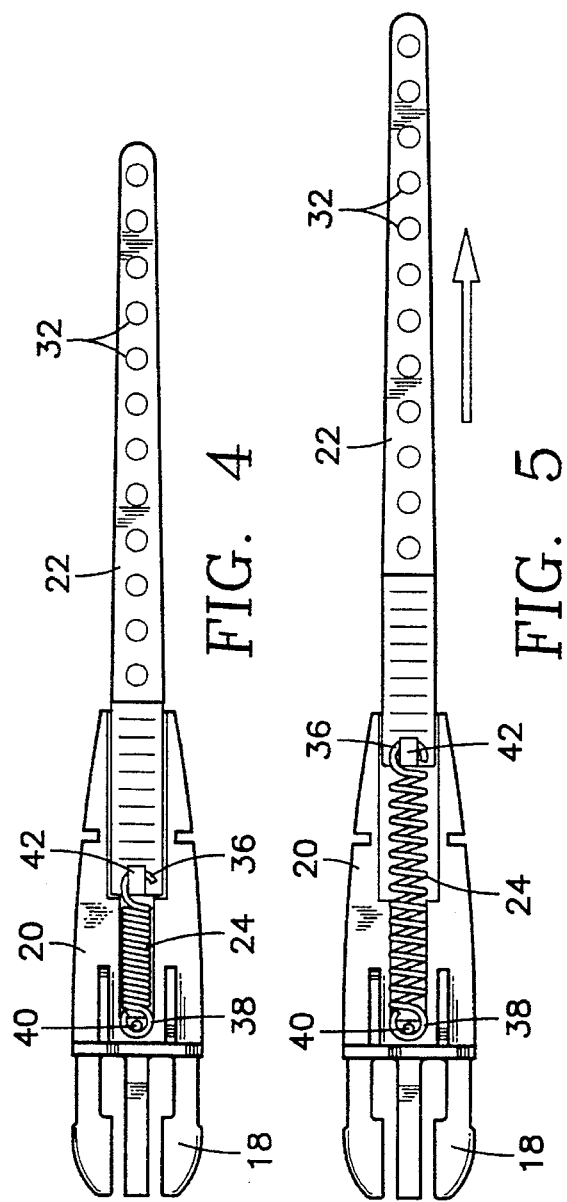
FIG. 4
FIG. 5
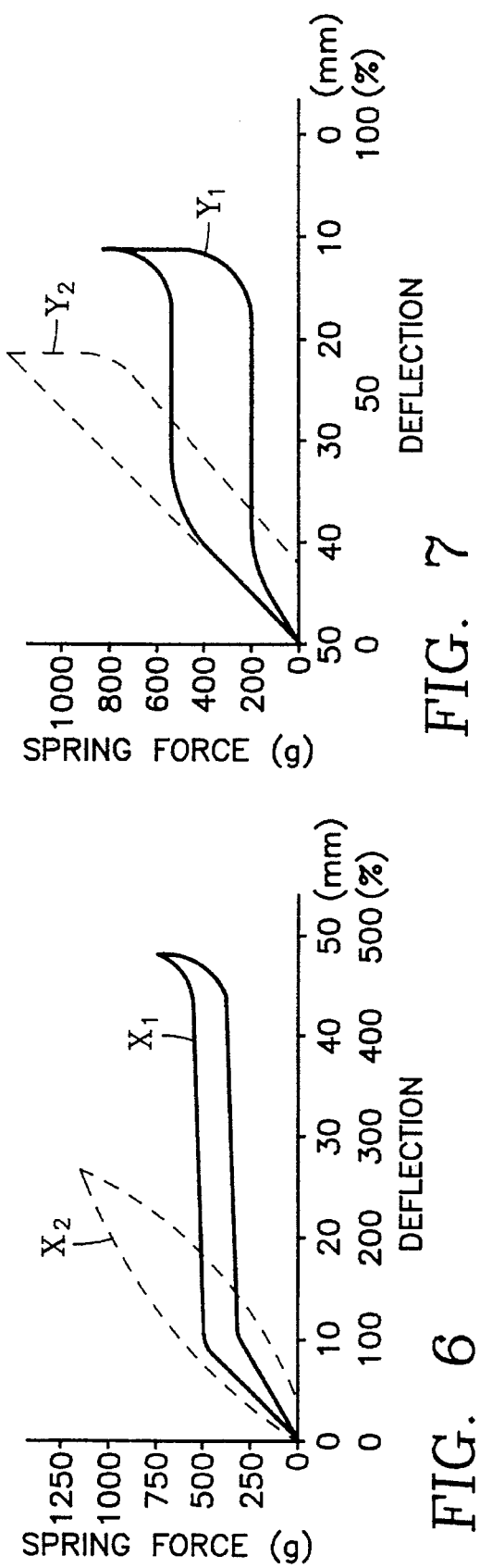
FIG. 7
FIG. 6

SUBSTANTIALLY CONSTANT FORCE COIL SPRING USABLE IN EXTRAORAL ORTHODONTIC APPLIANCE

BACKGROUND OF THE INVENTION

1. Field of the Invention

The field of this invention relates to orthodontic devices and more particularly to a coil spring which is to be used in an extraoral orthodontic appliance where the coil spring is constructed so as to impart a substantially constant force over the entire range of deflection of the spring.

2. Description of the Prior Art

Orthodontics is a specialty of dentistry which is concerned with the treatment of malpositioned teeth and the correction of improper relationships of the teeth and dental arches. It is common to utilize intraoral orthodontic appliances and extraoral orthodontic appliances to correct improperly positioned teeth. It is also common in both intraoral and extraoral appliances to use some form of spring mechanism so that a force can be applied to the teeth.

In the past, the force producing means for intraoral and extraoral orthodontic appliances has been coil springs, rubberbands and elasticized cloth. Rubberbands lose their force within 24 hours and must be replaced frequently. The patients are required to replace the rubberbands every day and may chose not to replace such a rubberband especially if the rubberband utilizes a higher force and therefore be more painful to the user. The result is when using rubberbands, treatment frequently progresses less efficiently than what it should be. The advantage of rubberbands is that they do impart a substantially constant force onto the teeth once the rubberband is deflected. Increase or decrease of deflection of the rubberband does not significantly alter the application force.

Elasticized cloth straps also have a constant force versus extension characteristics. However, such elasticized cloth straps also need to be frequently replaced, usually within two to three weeks of usage.

The most common type of force producing device is the coil spring. Coil springs that have been commonly used in the past are stainless steel springs. The advantage of springs as a force producing device is that they almost never require replacement during the entire length of time of usage. The disadvantage of most springs that are in common use is that they do not apply a constant force over different deflections. Deflection increases and decreases when the user talks or moves his or her head. Therefore, when using the conventional stainless steel type of spring, the force that is applied is constantly changing. Orthodontists feel that constant force application moves the teeth more efficiently than variable forces. Also variable forces can cause pain especially if the force significantly increases momentarily.

The advantages of using a constant force spring in an orthodontic headgear has been previously known. Reference is to be had to the U.S. Pat. No. 4,849,032 by Kozo Kawaguchi. However, the aforesaid patent has dealt only with the inclusion of constant force springs within an intraoral appliance. When dealing intraorally the springs are quite small in size and therefore of a substantially less force than what would be used in an extraoral appliance. Therefore, the problems encountered in designing such springs for intraoral orthodontic appliances are substantially different than what are encountered in designing constant force springs in an extraoral orthodontic appliance. There is a U.S. Pat. No. 4,264,302 by Roger Wolk et al. which is directed to an extraoral orthodontic appliance which uses a constant force flat spring assembly. The spring of the present invention can be manufactured more economically than the flat spring assembly of Wolk et al.

SUMMARY OF THE INVENTION

An extraoral orthodontic appliance comprising a tension applying mechanism for use about the head of a human for applying force to the teeth of the human through teeth mounted braces for the purpose of achieving proper occlusion. Within orthodontics it is common to use extraoral devices to apply a steady continuous force to intraoral devices for the purposes of assisting in obtaining or maintaining a proper occlusion. The application of the steady continuous force is generally by means of some type of biasing device. The biasing device within the present invention comprises a coil spring, that coil spring being constructed from a superelastic, shape-memory alloy wire. The wire is wound into a coil having a diameter of approximately 0.02 inches. The length of the coil is between 0.1875 inches and 2.5 inches. The diameter of the coil is between 0.05 inches and 0.45 inches. The spring force can be selected to be within the range of 375 to 800 grams. The selected spring force, according to a specific installation, will remain at the selected level regardless of head movement of the user which includes talking.

The primary objective of the present invention is to utilize a constant force coil spring in an extraoral orthodontic appliance in order to apply a constant force to the teeth of the wearer.

Another objective of the present invention is that by utilizing a constant force coil spring, the extraoral orthodontic appliance is easier to manufacture and easier to assemble.

Another objective of the present invention is that by utilizing a constant force coil spring, the overall size of the extraoral orthodontic appliance can be made smaller and more compact.

BRIEF DESCRIPTION OF THE DRAWINGS

FIG. 1 is a side view of a typical high pull, extraoral, orthodontic appliance showing the appliance in its normally installed position which includes the superelastic coil spring of this invention;

FIG. 2 is a side of a typical, neck pull, extraoral, orthodontic appliance showing the appliance in its normally installed position which includes the superelastic coil spring of this invention;

FIG. 3 is a longitudinal cross-sectional view through one of the side pull assemblies utilized in conjunction with either of the orthodontic appliances of FIGS. 1 and 2 showing the position of a tension coil spring at the at-rest position within the side pull assembly;

FIG. 4 is a side cross-sectional view through the side pull assembly utilized within the extraoral orthodontic appliance of the present invention showing the tension coil spring in the non-tensioned (at-rest) position of FIG. 3;

FIG. 5 is a side cross-sectional view similar to FIG. 4 but showing the tension coil spring in a maximum tensioned positioned;

FIG. 6 is a spring force/deflection graph of a superelastic tension coil spring constructed in accordance with the parameters of the present invention showing the graph in comparison to the graph for a conventional (non-superelastic) tension coil spring;

FIG. 7 is a spring force/deflection graph for a superelastic compression coil spring constructed in accordance with the parameters of the present invention showing the graph in comparison to the graph for a conventional non-superelastic compression coil spring;

FIG. 8 is a typical representation of a tension coil spring that would be usable within the present invention; and FIG. 9 is a typical representation of a compression coil spring that would be usable within the present invention.

DETAILED DESCRIPTION OF THE PREFERRED EMBODIMENT

Referring particularly to the drawings, there is shown in FIG. 1 the high pull orthodontic appliance 10 of this invention. The orthodontic appliance 10 includes a head harness 12 which has attached at each end thereof a female fastener 14. It is to be understood that there is to be a female fastener located on each side of the head 16 of the user. Each female fastener 14 is to be releasably connected to a male fastener 18. Each male fastener 18 is fixedly mounted on a housing 20. Extending from the housing 20 is a strap 22. The straps 22 are lineally movable relative to the housing 20 but when released, will automatically retract to an at-rest position. The at-rest position would be with the tension coil spring 24 located in its shortest length which is shown in FIG. 4.

Referring particularly to FIG. 2 there is shown the low pull or cervical orthodontic appliance 11 which does not use a harness but instead connects together, by a releasable male/female fastener, a pair of housings with only housing 13 being shown. The housing 13 that is shown connects to a female fastener 15 which in turn connects with a male fastener 17. A strap 21 protrudes from housing 13 with it being understood that the housing not shown has a similar strap.

Each pair of straps 22 are to be connected to a face bow 28. Similarly, each pair of straps 21 are to be connected to a face bow 28. The face bow 28 generally comprises a section of wire which is to be locked into place with the orthodontic braces (not shown) located within the mouth 30 of the user. The reason for the holes 32 on each strap 22 is so as to provide for various connecting points for the face bow 28 so as to permit adjustability according to individual requirements. When the straps 21 and 22 are connected to the face bow 28, the spring 24 will be expanded similar to a position that is shown in FIG. 5 of the drawings. This will mean that the spring 24 applies a biasing force onto the face bow 28 with this biasing force being applied to the orthodontics mounted within the mouth 30.

Adhesively secured to the back side of each housing 13 and 20 is a foam pad 34. The function of the foam pad 34 is to provide a soft resilient surface that will be in contact with the side of the head 16 of the wearer.

Spring 24 is shown in FIG. 6. Spring 24 is a tension spring which includes hooked ends 36 and 38. Hooked end 36 is to connect with a protuberance 40 mounted on the housing 13 or 20. The hooked end 38 connects with protuberance 42 which is mounted on the inner end of the strap 21 or 22. Therefore, movement of the strap 21 and 22 relative to their respective housing 13 and 20 will result in stretching of the spring 24. It is to be understood that in certain environments that instead of a tension spring 24, there may be utilized a compression spring 44 which is shown in FIG. 7. Appropriate modification of the structure within housing 13 and 20 would be necessary to accommodate a compression spring.

Shown in FIG. 6 is a spring force/deflection curve for a tension coil spring 24 as compared to that for a conventional stainless steel coil spring. The coil spring 24 is to be constructed of superelastic alloy wire such as nickel titanium alloy known as Nitinol (tradename). The spring 24 could also be manufactured with other superelastic materials such as titanium nickel, nickel aluminum, iron platinum, copper zinc, copper zinc gallium, copper aluminum nickel, copper tin, titanium nickel copper, titanium nickel iron, gold cadmium, silver cadmium, copper zinc aluminum, copper zinc tin and copper gold zinc. The force deflection curve for the superelastic spring 24 is shown as curve $X_1$. The force deflection curve for a typical stainless steel spring is shown as curve $X_2$. As can be seen in FIG. 6, the spring 24 imparts a substantially constant spring force throughout a relatively wide range of deflection which is known as a superelastic zone of deflection. This relatively constant spring force occurs from a deflection of about ten millimeters all the way to sixty millimeters while with a conventional stainless steel type spring shown as curve $X_2$, the spring force increases sharply with increased deflection. As a result, the coil spring 24 can be employed to impart a predetermined and substantially constant spring force throughout the entire movement of a tooth unlike conventional springs which frequently change.

Referring particularly to FIG. 7, it can be seen there is depicted a similar force deflection curve for the superelastic compression spring 44. The curve for the spring 44 is shown as $Y_1$ with $Y_2$ being a typical force deflection curve for a stainless steel type of spring. Again the use of the superelastic materials has created a substantially constant spring force over the entire range of deflection which is from forty millimeters to about ten millimeters.

The main distinction of the present invention over that of other superelastic springs within the prior art has been that the coil springs 24 and 44 are designed to be used on extraoral orthodontic equipment. The springs in order to be effective have to be operable at a spring force which is substantially above intraoral orthodontic equipment. It is thus to be seen that both coil springs 24 and 44 operate above four hundred grams of force. By varying of size of the spring, the force can be varied between 375 and 800 grams. A typical size for the tension spring 24 would be to utilize a wire diameter of about 0.020 inches with a coil diameter of 0.05 inches to 0.35 inches. The length of the spring 24 (that is inside of the hooks 36 and 38) is to be between 0.1875 inches and 1.5 inches. For the compression spring 44 shown in FIG. 7, again the wire diameter is to be about 0.020 inches with a coil diameter of 0.05 inches to 0.45 inches. The length of the spring 44 is to be between 0.3 inches and 2.5 inches.

What is claimed is:

1. In an extraoral orthodontic appliance, a coil spring used for imparting forces to be applied against the teeth, said coil spring comprising:

a superelastic, shape-memory alloy wire wound into a coil, said wire having a wire diameter of 0.02 inches, said coil having a spring force selected to be within the range of 375 to 800 grams, said spring force to be substantially constant when said coil spring is installed in an orthodontic appliance regardless of movement of the user.

2. The extraoral orthodontic appliance as defined in claim 1 wherein:

said coil having a length and a coil diameter, said coil diameter being between 0.05 inches and 0.45 inches.

3. The extraoral orthodontic appliance as defined in claim 2 wherein:

said length being between 0.1875 inches and 2.5 inches.

\* \* \* \* \*